United States Patent [19]

Watanabe et al.

[11] Patent Number: 4,480,000
[45] Date of Patent: Oct. 30, 1984

[54] ABSORBENT ARTICLE

[75] Inventors: Isao Watanabe; Toshinobu Kashiwada, both of Chiba; Hiroshi Suzuki, Sagamihara; Junji Yoshii, Atsugi, all of Japan

[73] Assignees: Lion Corporation, Tokyo; Anne Company, Ltd., Kanagawa, both of Japan

[21] Appl. No.: 388,632

[22] Filed: Jun. 15, 1982

[30] Foreign Application Priority Data

Jun. 18, 1981 [JP] Japan ................................ 56-94178

[51] Int. Cl.$^3$ ............................................. A61F 13/00
[52] U.S. Cl. .................................... 428/284; 428/286; 428/287; 428/288; 428/298; 428/913; 604/370; 604/378; 604/385
[58] Field of Search ............... 428/284, 286, 287, 298, 428/288, 913; 604/370–374, 378, 379, 385

[56] References Cited

U.S. PATENT DOCUMENTS

| | | | |
|---|---|---|---|
| 3,545,442 | 12/1970 | Wicker et al. | 604/370 |
| 4,069,821 | 1/1978 | Fitzgerald et al. | 604/379 |
| 4,307,721 | 12/1981 | Tsuchiya et al. | 428/212 X |
| 4,324,246 | 4/1982 | Mullane et al. | 604/370 |
| 4,324,247 | 4/1982 | Aziz | 604/371 |

*Primary Examiner*—George F. Lesmes
*Assistant Examiner*—Nancy A. B. Swisher
*Attorney, Agent, or Firm*—Armstrong, Nikaido, Marmelstein & Kubovcik

[57] ABSTRACT

Improved absorbent articles such as sanitary napkins and disposable diapers are provided. The absorbent articles have (1) an absorbent core layer, (2) a barrier covering the lateral faces and underneath face of the absorbent core layer, (3) a web placed on the top of the absorbent core layer, and (4) a nonwoven fabric wrapped around the above-mentioned (1), (2) and (3). The nonwoven fabric is comprised of 10–70 wt. % of a regenerated cellulose fiber, 5–60 wt. % of a polyester fiber and 25–75 wt. % of a heat-bondable composite polyolefin fiber, and the web is predominantly comprised of a polyester fiber. The absorbent articles absorb a body fluid at an enhanced rate and have a feeling of dryness even after such absorption.

6 Claims, 2 Drawing Figures

ABSORBENT ARTICLE

BACKGROUND OF THE INVENTION

(1) Field of the Invention

This invention relates to an improvement in absorbent articles which are used, for example, as sanitary napkins and disposable diapers and are characterized by absorbing menstrual fluid, urine, and other body fluids at an extremely enhanced rate and having, after the absorption of a body fluid, a feeling of dryness.

(2) Description of the Prior Art

It is known that conventional absorbent articles such as sanitary napkins have as a top cover a nonwoven fabric made of a blend of a heat-bondable composite polyolefin fiber and another fiber. It is recognized that if such a top cover is made of a well-balanced blend of a hydrophobic fiber and a hydrophilic fiber, the top cover absorbs a body fluid at an enhanced absorption rate, the absorbed body fluid does not seep out of the absorbent article, and, thus, the absorbent article maintains a feeling of dryness. It is naturally desirable that the absorption rate be as high as possible and that the absorbent feel as dry as possible after the absorption of a body fluid in order to mitigate the physiological and physical discomfort and the unpleasant feeling accompanying menses. Thus, enhancement of the absorption rate and the feeling of dryness has heretofore been and is still greatly desired.

SUMMARY OF THE INVENTION

It is, therefore, a primary object of the present invention to provide absorbent articles exhibiting an enhanced absorption rate and having, after the absorption of a body fluid, an enhanced feeling of dryness.

Other objects and advantages of the present invention will be apparent from the following description.

In accordance with the present invention, there is provided an absorbent article comprising (1) an absorbent layer, (2) a barrier covering the lateral faces and underneath face of the absorbent layer, (3) a web placed on the top of the absorbent layer and (4) a nonwoven fabric wrapped around the absorbent layer, the barrier and the web, wherein said nonwoven fabric comprises, based on the weight of the nonwoven fabric, 10 to 70% by weight of a regenerated cellulose fiber, 5 to 60% by weight of a polyester fiber, and 25 to 75% by weight of a heat-bondable composite polyolefin fiber, and said web is predominantly comprised of a polyester fiber.

DESCRIPTION OF THE PREFERRED EMBODIMENTS

Figure 1:
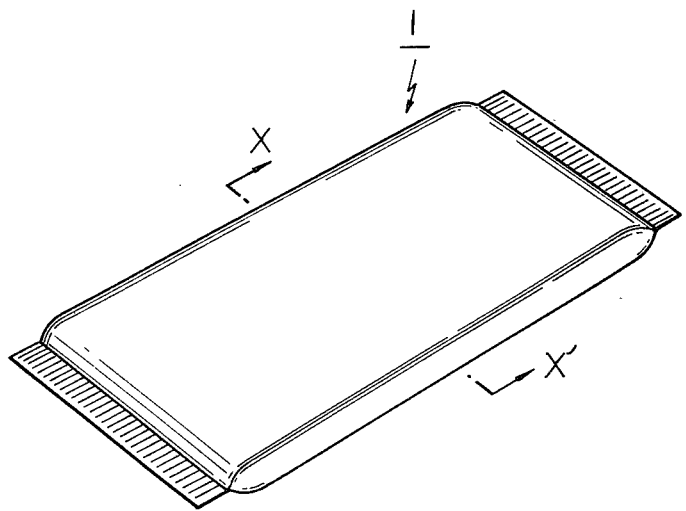
FIG. 1 is a perspective view of an absorbent article of the present invention.
Figure 2:
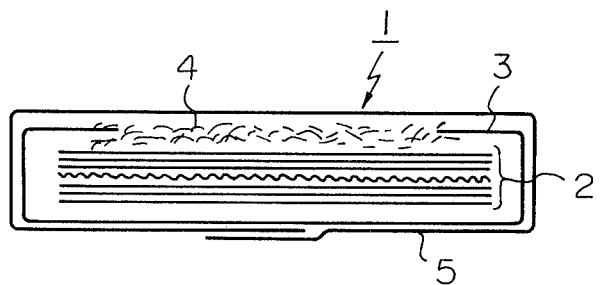
FIG. 2 is an enlarged sectional view taken along the line X—X' in FIG. 1.

Referring to FIGS. 1 and 2 wherein a sanitary napkin is illustrated as an example of the absorbent article of the present invention, the sanitary napkin 1 is comprised of an absorbent layer 2 located in the core portion, a barrier 3 covering the lateral faces and underneath face of the absorbent layer 2, a web 4 placed on the top of the absorbent layer 2, and a nonwoven fabric 5 wrapped around the absorbent layer 2, the barrier 3, and the web 4.

By the term "web" used herein is meant a mass of fibers in the form of a sheet which is made up of non-interlaced and non-bonded fibers.

One main feature of the present invention resides in the nonwoven fabric used as a top cover of the absorbent article. The nonwoven fabric is made of a blend of a regenerated cellulose fiber, a polyester fiber and a heat-bondable polyolefin composite fiber. It is preferable that the regenerated cellulose fiber have a fineness of 1 to 6 deniers, more preferably 1.5 to 3 deniers, and a length of 1.5 to 7 cm, more preferably 3 to 5 cm. As the regenerated cellulose fiber, there can be mentioned a viscose rayon.

It is preferable that the polyester fiber have a fineness of 1 to 7 deniers, more preferably 1.5 to 4 deniers, and a length of 1.5 to 7 cm, more preferably 3 to 5 cm. As the polyester fiber, there can be mentioned a polyethylene terephthalate fiber and other commercially available polyester fibers for apparel use.

The heat-bondable composite polyolefin fiber preferably possess either a sheath-core structure comprising a high-melting polyolefin core ingredient surrounded by a low-melting polyolefin sheath ingredient or a side-by-side structure comprising a high-melting polyolefin ingredient and a low-melting polyolefin ingredient. A preferable heat-bondable composite polyolefin fiber is composed of polypropylene as the high-melting polyolefin ingredient and polyethylene as the low-melting polyolefin ingredient and is commercially available, for example, under the tradename of "ES fiber" (manufactured by Chisso K.K.). It is preferable that the heat-bondable composite polyolefin fiber have a fineness of 1 to 20 deniers, more preferably 1.5 to 7 deniers, and a length of 1 to 10 cm, more preferably 4 to 7 cm. The proportion of the three fibers in the nonwoven fabric should be, based on the weight of the nonwoven fabric, as follows: the regenerated cellulose fiber, 10 to 70%, preferably 30 to 60%, by weight; the polyester fiber, 5 to 60%, preferably 5 to 40%, by weight; and the hot-bondable composite polyolefin fiber, 25 to 75%, preferably 30 to 65%, by weight.

The nonwoven fabric used as a top cover of the absorbent article of the present invention may be prepared by a process wherein the above-mentioned three fibers are uniformly blended and made into a sheet form, and the sheet is heated at a temperature of 120° to 150°, whereby the composite polyolefin fibers are bonded with each other at their intersecting points. The nonwoven fabric, so prepared, has a basis weight of 10 to 35 $g/m^2$, preferably 13 to 18 $g/m^2$, and a density of 0.01 to 0.1 $g/cm^3$, preferably 0.05 to 0.07 $g/cm^3$.

Another main feature of the present invention resides in the web, which is predominantly made up of a polyester and is interposed between the above-mentioned nonwoven fabric and the absorbent layer. If no web is interposed between the nonwoven fabric and the absorbent layer or if a conventional web made of a rayon staple fiber is interposed, between the nonwoven fabric and the absorbent layer, the intended enhanced absorption rate and feeling of dryness cannot be attained. It has not clearly been elucidated yet but it is presumed that the intended enhanced absorption rate and feeling of dryness are due to the fact that a polyester fiber is contained in both the nonwoven fabric and the web.

The polyester web should be bulky and preferably possess a basis weight of 10 to 50 $g/m^2$, more preferably 15 to 30 $g/m^2$, and a density of 0.001 to 0.04 $g/cm^3$, more preferably 0.003 to 0.02 $g/cm^3$. As the polyester fiber, a polyethylene terephthalate fiber and other commercially available polyester fibers for apparel use can be used. The polyester fiber may be either tow or staple. If a polyester fiber in the form of two is used, it is preferable that the fiber be crimped so that it has a high bulkiness and good workability. If a polyester fiber in the form of staple is used, it is preferable that the fiber have a length of 1 to 6 cm, more preferably 1 to 3 cm.

The absorbent layer and the barrier in the absorbent article of the present invention may be conventional. Namely, the absorbent layer may be made of, for example, cellulose pulp, absorbing paper, a high polymeric absorbent material, or a combination of these materials. The barrier may be made of, for example, polyethylene film, polyethylene-laminated paper, polyvinyl alcohol film, or water-repellent paper.

The absorbent article of the present invention, which is characterized by having the specified polyester web on the top of the absorbent core layer and further by having the specified nonwoven fabric wrapped around the entire body of the absorbent article, is superior to other absorbent articles which have the same absorbent core layer but a different web and/or nonwoven fabric as follows. Namely, the absorbent article of the present invention absorbs menstrual fluid, urine, and other body fluids at an extremely enhanced rate, and the absorbed body fluid does not readily seep out of the absorbent article. Thus, the absorbent article has a feeling of dryness even after the absorption of a body fluid, and the absorbent article does not become stuffy. Furthermore, the nonwoven fabric used as the top cover is soft and does not give a feeling of physical discomfort. Therefore, when the absorbent article is used as a sanitary napkin or a disposable diaper, it has a good feel and is comfortable for the wearer.

The invention will be further illustrated by the following examples.

EXAMPLES

Sanitary napkins having a laminated structure similar to that shown in FIGS. 1 and 2 were prepared. The napkins consisted of (1) an absorbent layer comprised of fleece-like pulp and three sheets of absorbent paper, (2) a polyethylene-laminated paper (barrier), (3) a web, and (4) a nonwoven fabric wrapped around the absorbent layer, the barrier and the web. The respective nonwoven fabrics and webs were made of the fibers shown in Table I below.

The rate of absorption of menstrual fluid, the amount of menstrual fluid which seeped out of the napkin and the feeling of dryness were determined as follows.

ADSORPTION RATE

An iron plate having a perforation in the center thereof and having a cylinder attached to the perforated portion was placed on each horizontally laid sanitary napkin specimen. A pressure of 8 g/cm$^2$ was applied to the specimen, and 10 ml of a simulated menstrual fluid containing 0.89% by weight of an electrolyte and having a surface tension of 42 dyne/sec was forced in one stroke through the cylinder into the specimen. The amount of time in which the simulated menstrual fluid was absorbed on the surface of the specimen was determined. The absorption rate was expressed in terms of such an amount of time (sec.).

AMOUNT OF MENSTRUAL FLUID SEEPED OUT

Two minutes after the determination of the absorption rate, a pile of 20 sheets of filter paper was superposed on the absorbed specimen and than a pressure of 50 g/cm$^2$ was uniformly applied thereto. The pressed specimen was maintained under this pressure for two minutes and then the amount of fluid which seeped out of the specimen onto the filter papers was measured.

FEELING OF DRYNESS

The feeling of dryness after the absorption of menstrual fluid was panel tested by twenty women from 18 to 24 years old, was evaluated according to the following five ratings, and was expressed by the average rating.

5: Very dry
4: Slightly dry
3: Moderate
2: Slightly wet
1: Very wet

The nonwoven fabrics used were made in a conventional manner from a viscose rayon staple fiber having a fineness of 2 deniers and a length of 5 cm, a polyethylene terephthalate staple fiber having a fineness of 2 deniers and a length of 5 cm, and a heat-bondable polypropylene/polyethylene composite staple fiber ("Polypro-ES fiber" supplied by Chisso K.K.) having a fineness of 3 deniers and a length of 6.4 cm. The nonwoven fabrics had a basis weight of 14 to 15 g/m$^2$ and a density of 0.06 g/cm$^3$.

The webs used were made from a polyethylene terephthalate staple fiber and a viscose rayon staple fiber, both of which had a fineness of 1.5 deniers and a length of 1.5 cm. The webs had a basis weight of 25 g/m$^2$ and a density of 0.004 g/cm$^3$.

The test results are shown in Table I below.

TABLE I

| No. | Composition or nonwoven fabric | | | Web | Absorption rate (sec.) | Amount of fluid that seeped out (g) | Feeling of dryness |
| --- | --- | --- | --- | --- | --- | --- | --- |
| | Cellulose fiber (%) | Polyester fiber (%) | Polyolefin fiber (%) | | | | |
| Example 1 | 10 | 25 | 65 | Polyester | 2.9 | 3.1 | 3.7 |
| Example 2 | 10 | 40 | 50 | " | 3.3 | 3.1 | 3.7 |
| Example 3 | 10 | 60 | 30 | " | 3.0 | 3.1 | 3.7 |
| Example 4 | 35 | 5 | 60 | " | 3.2 | 3.2 | 3.9 |
| Example 5 | 35 | 25 | 40 | " | 2.8 | 3.2 | 4.1 |
| Example 6 | 35 | 40 | 25 | " | 2.9 | 3.1 | 3.6 |
| Example 7 | 55 | 5 | 40 | " | 3.7 | 3.0 | 3.9 |
| Example 8 | 55 | 20 | 25 | " | 3.1 | 3.0 | 3.6 |
| Example 9 | 70 | 5 | 25 | " | 3.5 | 3.0 | 3.7 |
| Comparative Example 1 | 10 | — | 90 | " | 4.7 | 3.8 | 3.1 |
| Comparative Example 2 | 50 | — | 50 | " | 4.9 | 3.9 | 3.2 |
| Comparative Example 3 | 75 | — | 25 | " | 4.3 | 3.9 | 2.8 |
| Comparative Example 4 | — | 50 | 50 | " | 5.6 | 3.4 | 3.0 |
| Comparative Example 5 | 80 | 10 | 10 | " | 4.0 | 3.7 | 2.1 |
| Comparative Example 6 | 50 | 40 | 10 | " | 4.2 | 3.6 | 2.5 |
| Comparative Example 7 | 10 | 80 | 10 | " | 5.1 | 3.3 | 2.6 |
| Comparative Example 8 | 35 | 25 | 40 | No web used | 4.8 | 7.5 | 1.7 |
| Comparative Example 9 | 35 | 25 | 40 | Viscose rayon | 5.5 | 6.1 | 2.8 |

We claim:

1. An absorbent article comprising (1) an absorbent layer, (2) a barrier covering the lateral faces and underneath face of the absorbent layer, (3) a web placed on the top of the absorbent layer and (4) a nonwoven fabric wrapped around the absorbent layer, the barrier and the web, characterized in that said nonwoven fabric comprises, based on the weight of the nonwoven fabric, 10 to 70% by weight of a regenerated cellulose fiber, 5 to 60% by weight of a polyester fiber and 25 to 75% by weight of a heat-bondable composite polyolefin fiber, and said web is predominantly comprised of a polyester fiber.

2. An absorbent article according to claim 1 wherein said web is made of polyester fibers and has a basis weight of 10 to 50 g/m$^2$.

3. An absorbent article according to claim 1 wherein said web has a density of 0.001 to 0.04 g/cm$^3$.

4. An absorbent article according to claim 1 wherein said nonwoven fabric comprises, based on the weight of the nonwoven fabric, 30 to 60% by weight of a regenerated cellulose fiber, 5 to 40% by weight of a polyester fiber and 30 to 65% by weight of a heat-bondable polyolefin composite fiber.

5. An absorbent article according to claim 1 or 4 wherein said nonwoven fabric has a basis weight of 10 to 35 g/m$^2$.

6. An absorbent article according to claim 1 or 4 wherein said nonwoven fabric has a density of 0.01 to 0.1 g/cm$^3$.

* * * * *